(12) United States Patent
Cheong et al.

(10) Patent No.: US 10,751,352 B2
(45) Date of Patent: Aug. 25, 2020

(54) PHARMACEUTICAL COMPOSITION FOR PREVENTING OR TREATING CANCER

(71) Applicant: HAIMBIO CO., LTD., Seoul (KR)

(72) Inventors: Jae Ho Cheong, Seoul (KR); Ki Cheong Park, Seoul (KR)

(73) Assignee: HAIMBIO CO., LTD. (KR)

( * ) Notice: Subject to any disclaimer, the term of this patent is extended or adjusted under 35 U.S.C. 154(b) by 91 days.

(21) Appl. No.: 16/104,291

(22) Filed: Aug. 17, 2018

(65) Prior Publication Data

US 2019/0343854 A1    Nov. 14, 2019

(30) Foreign Application Priority Data

May 9, 2018   (KR) ........................ 10-2018-0052950

(51) Int. Cl.
| | | |
|---|---|---|
| *A61K 31/7004* | (2006.01) | |
| *A61P 35/00* | (2006.01) | |
| *A61K 31/155* | (2006.01) | |
| *A61K 31/365* | (2006.01) | |

(52) U.S. Cl.
CPC ........ *A61K 31/7004* (2013.01); *A61K 31/155* (2013.01); *A61K 31/365* (2013.01); *A61P 35/00* (2018.01)

(58) Field of Classification Search
None
See application file for complete search history.

(56) References Cited

FOREIGN PATENT DOCUMENTS

KR   10-2018-0055423   *   5/2018   ......... A61K 31/7004

OTHER PUBLICATIONS

Pei, S., Minhajuddin, M., D'Alessandro, A., Nemkov, T., Stevens, B. M., Adane, B., . . . & Ashton, J. M. (2016). Rational design of a parthenolide-based drug regimen that selectively eradicates acute myelogenous leukemia stem cells. Journal of Biological Chemistry, 291(42), 21984-22000. (Year: 2016).*
Metts, J., Bradley, H. L., Wang, Z., Shah, N. P., Kapur, R., Arbiser, J. L., & Bunting, K. D. (2017). Imipramine blue sensitively and selectively targets FLT3-ITD positive acute myeloid leukemia cells. Scientific reports, 7(1), 4447. (Year: 2017).*
Sabnis, H. S., Bradley, H. L., Tripathi, S., Yu, W. M., Tse, W., Qu, C. K., & Bunting, K. D. (2016). Synergistic cell death in FLT3-ITD positive acute myeloid leukemia by combined treatment with metformin and 6-benzylthioinosine. Leukemia research, 50, 132-140. (Year: 2016).*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*

* cited by examiner

*Primary Examiner* — Dale R Miller
(74) *Attorney, Agent, or Firm* — Sheridan Ross P.C.

(57) ABSTRACT

The present invention relates to a pharmaceutical composition for preventing or treating cancer, which contains a glucose uptake inhibitor and a sesquiterpene lactone. The pharmaceutical composition according to the present invention is capable of effectively inhibiting the proliferation of not only cancer cells but also cancer stem cells, thereby preventing and/or treating cancer, and furthermore, preventing the resistance, metastasis and recurrence of cancer.

6 Claims, 20 Drawing Sheets

Specification includes a Sequence Listing.

PHARMACEUTICAL COMPOSITION FOR PREVENTING OR TREATING CANCER

CROSS-REFERENCE TO RELATED APPLICATION(S)

This application claims priority to Korean Patent Application No. 10-2018-0052950, filed on May 9, 2018, the disclosure of which is incorporated herein by reference in its entirety.

REFERENCE TO A SEQUENCE LISTING

This application contains a Sequence Listing submitted electronically as a text file by EFS-Web. The text file, named "POPB187220US-SEQ.txt", has a size in bytes of 2000 bytes, and was recorded on 14 Aug. 2018. The information contained in the text file is incorporated herein by reference in its entirety pursuant to 37 CFR § 1.52(e)(5).

BACKGROUND OF THE INVENTION

Field of the Invention

The present invention relates to a pharmaceutical composition capable of effectively preventing or treating cancer by co-administering a glucose uptake inhibitor and a sesquiterpene lactone.

Description of the Related Art

Cancer is one of the most common causes of death worldwide. Approximately 10 million new cancer cases occur each year, and cancer accounts for approximately 12% of all death causes, which is the third leading cause of death.

Among cancers, breast cancer is the most common malignant tumor in women, and causes more than 40,000 deaths annually. Early diagnosis of cancer is very important, but the survival rate of cancer patients has not improved when cancer has progressed significantly or metastasized despite treatment with many already known anticancer agents. Chemotherapy, a typical anticancer therapy, is the most efficient therapy which is currently used alone or in combination with other therapies, such as radiotherapy, in order to treat cancer. The efficacy of cancer treatment drugs in chemotherapy depends on their ability to kill cancer cells, but the use of these drugs has a problem in that these drugs can also act on normal cells in addition to cancer cells.

Cancer stem cells have the ability to self-renew indefinitely. The hypothesis that tumors originate from stem cells was confirmed, as it was reported in the late 1990s that a group of cells capable of functioning as cancer stem cells in acute myelogenous leukemia were transplanted into immunosuppressed mice and human leukemia was reproduced in the mice. Since then, cancer stem cells have been proven to exist in breast cancer, and the presence of stem cells in solid carcinomas has also been confirmed.

Various heterogeneities of malignant tumors are consistent with various differentiation potentials of stem cells, and the drug resistance of cancer cells, which is constantly expressed despite many target therapies, is consistent with the fundamental characteristics of stem cells. Accordingly, the development of tumors can be considered associated with stem cells, and cancer stem cells can be a new field of targeted therapy.

Various therapeutic methods have been devised based on the cancer stem cell hypothesis. Among them, the most widely known method is a method based on the self-renewal pathway of cancer stem cells. In this therapy, it is important to target only the self-renewal of cancer stem cells while maintaining the self-renewal of normal stem cells. For example, notch signaling is induced by the enzyme gamma secretase, and when an inhibitor against gamma secretase (i.e., a gamma secretase inhibitor) is used against breast cancer overexpressing Notch1, an anti-tumor effect can be achieved. In addition, it has recently been reported that when the hedgehog signaling system is targeted, an anticancer effect is obtained. Specifically, it was reported that when cyclopamine, a hedgehog inhibitor, was administered to a tumor xenograft animal, the tumor volume was dramatically reduced. In addition, the gamma secretase is known to be involved in PI3K/AKT, MAPK and JAK2/STAT3 signaling pathways.

However, there have been many limitations in studies on cancer stem cells so far, and the role of cancer stem cells in the formation or maintenance of tumors has not yet to be established. In order to efficiently perform a therapy that targets only cancer stem cells without damaging normal stem cells, knowledge and understanding of molecular biological characteristics important for the maintenance and regulation of cancer stem cells or the regulatory pathways thereof are required.

To date, there have been few studies on anticancer drugs or natural extracts that directly target cancer stem cells. In the prior art, various studies focused on inhibiting cancer stem cells or inhibiting upstream signaling proteins in cancer stem cells to inhibit the cancer stem cells have been conducted as experiments on inhibiting direct target genes of cancer stem cells. However, these targeting experiments have encountered many difficulties due to tumor gene mutations or protein mutations in many tumor patients.

Thus, improving the selectivity of drugs for cancer stem cells will certainly make it possible to use the drugs at lower doses by increasing the chemotherapeutic efficacy of the anticancer drugs. Therefore, in order to treat and prevent cancer, an improved approach capable of selectively inhibiting the growth of cancer stem cells is required.

SUMMARY OF THE INVENTION

It is an object of the present invention to provide a pharmaceutical composition capable of preventing and/or treating cancer by effectively inhibiting the growth of cancer cells.

Another object of the present invention is to provide a pharmaceutical composition not only capable of preventing and/or treating cancer, but also capable of preventing the resistance, metastasis and recurrence of cancer, by effectively inhibiting the growth of cancer stem cells.

The present inventors have found that co-administration of a glucose uptake inhibitor, particularly 2-deoxyglucose (2DG), and a sesquiterpene lactone, particularly thapsigargin, effectively inhibits the growth of not only cancer cells, but also cancer stem cells, thereby completing the present invention.

One embodiment of the present invention is directed to a pharmaceutical composition for preventing or treating cancer, which contains, as active ingredients, a glucose uptake inhibitor and a sesquiterpene lactone.

In the present invention, the "glucose uptake inhibitor" is not particularly limited and may be any compound that inhibits the uptake of glucose (that is an energy source for cells) to induce nutrient deprivation and/or metabolic energy exhaustion-associated endoplasmic reticulum stress conditions, thereby inhibiting cell growth and inducing expression of plasma membrane Ca' ATPase (PMCA) in cancer stem cells. The "glucose derivative" is a glucose-like compound obtained by modifying a portion of glucose, and it is not particularly limited and may be any compound which acts competitively with normal glucose to inhibit glucose uptake. In the present invention, the glucose uptake inhibitor may preferably be a glucose derivative, more preferably 2-deoxyglucose (2DG).

In the present invention, the "sesquiterpene lactones" are compounds that are sesquiterpenoids and contain a lactone ring. They are found in many plants, and some may also be found in corals such as *Maasella edwardsi*. The sesquiterpene lactones may be classified into germacranolides, heliangolides, guaianolides, pseudoguaianolides, hypocretenolides, eudesmanolides, and the like. However, preferably, the sesquiterpene lactone that is used in the present invention may be one or more selected from the group consisting of thapsigargin, artemisinin and parthenolide. More preferably, the sesquiterpene lactone may be thapsigargin.

The pharmaceutical composition according to the present invention may, if necessary, further contain a biguanide-based compound.

In the present invention, the biguanide-based compound is not particularly limited and may be any biguanide-based compound that interferes with intracellular energy production to induce a nutrient deficiency-like state. Preferably, it may be a biguanide-based drug for treating diabetes. More preferably, the biguanide-based compound may be one or more selected from the group consisting of metformin, phenformin, and buformine. Most preferably, it may be metformin.

When the pharmaceutical composition according to the present invention further contains the biguanide-based compound in addition to the glucose uptake inhibitor and the sesquiterpene lactone, it can more effectively inhibit the growth of cancer cells and cancer stem cells.

In general, the term "cancer stem cells" comprehensively refers to cancer cells having the ability to self-renew or differentiate, which is characteristic of stem cells.

The "cancer" refers to or describes the physiological condition in mammals that is typically characterized by unregulated cell growth. Cancer to be treated or prevented may be, depending on the site of development thereof, breast cancer, uterine cancer, fallopian tube cancer, ovarian cancer, gastric cancer, brain cancer, rectal cancer, colorectal cancer, small intestine cancer, esophageal cancer, lymphoma, gallbladder cancer, lung cancer, skin cancer, renal cancer, bladder cancer, blood cancer, pancreatic cancer, prostate cancer, thyroid cancer, endocrine cancer, oral cancer, liver cancer, or the like. Preferably, the cancer may be breast cancer. In addition, the cancer is not limited thereto and may be any type of cancer whose progression (such as differentiation and/or proliferation of tumors) is dependent on cancer stem cells as described in the present invention.

It was reported that these cancer stem cells capable of differentiating into cancer cells account for about 1 to 2% of malignant tumor tissue, and have self-renewal ability, which is characteristic of normal stem cells, as well as the pluripotent potential to differentiate into other cells, but increase in number through cell division activation due to abnormalities in their self-regulatory function, and self-differentiate into malignant tumor cells.

Since cancer stem cells were found in leukemia in 1997 (Blood, 1997), there has been evidence that cancer stem cells are also present in breast cancer (PNAS, 2003), brain tumors (Nature, 2004), prostate cancer (Cancer Res, 2005), colorectal cancer (Nature, 2007) and melanoma (Nature, 2008). In addition, a small number of cancer stem cells contained in tumors have been considered as the main cause of tumor malignancy, anti-cancer drug resistance, and cancer recurrence.

Cancer stem cells contain markers that distinguish these cells from other cells. As cancer stem cell markers, a variety of carcinoma-specific cancer stem cell markers as shown in Table 1 below are known.

TABLE 1

| Carcinoma | Cancer stem cell marker | Source |
|---|---|---|
| Glioblastoma | CD133 | |
| Kidney cancer | CD105, CD133 | Contemp Oncol (Pozn). 2015; 19(1A): A44-A51 |
| Thyroid cancer | ABCG2, MRP1, LRP and CXCR4 | J Clin Pathol. 2014 Feb; 67(2): 125-33 |
| Acute myeloid leukemia (AMM) | CD34+/CD38− | |
| Multiple myeloma | CD133− | |
| Breast cancer | CD44+/CD24−/low | Breast Cancer Res. 2007; 9(3): 303 |
| Colorectal cancer | CD133+ | |
| Prostate cancer | CD44+/α2β1hi/CD133+ | |
| Melanoma | ABCB5+ | |

Cancer stem cells whose growth can be inhibited according to the present invention may include all the above-listed cancer stem cells, but may particularly be breast cancer stem cells.

The above-described cancer stem cells constantly self-renew, can form a tumor in an experimental animal model even when they are present in small numbers (less than a thousand cells), and possess potency as malignant tumor cells. In addition, these cancer stem cells are surprisingly resistant to anticancer drug therapy and radiation therapy, which are cancer treatment methods, and thus the removal of cancer stem cells is increasingly recognized as a barometer of success or failure of cancer treatment. Recently, it has been recognized that even when cancer cells are killed using several conventional therapeutic methods, including surgery, radiotherapy, anticancer chemotherapy and the like, cancer can be recur from the remaining cancer stem cells if all the cancer stem cells cannot be killed. In order to prevent this cancer recurrence, there is an increasing interest in the development of a chemotherapy that targets cancer stem cells having the capability to regenerate tumors, as well as a treatment protocol for treating cancer based on the chemotherapy.

It is suggested that growth and differentiation of stem cells in normal tissue are regulated by a self-renewal mechanism, but cancer stem cells are enriched rapidly by the activation of abnormal self-renewal and maintenance pathways due to the influence of the surrounding tumor microenvironments, and thus become malignant and acquire resistance to anti-cancer therapy, ultimately leading to cancer recurrence. However, studies on the identification of tumor microenvironmental factors controlling the enrichment and maintenance of cancer stem cells and on the detailed mechanism of the interaction therebetween have not yet been conducted.

As used herein, the term "preventing" refers to all actions that block the occurrence of cancer symptoms or inhibit or delay the progression of cancer symptoms by using the pharmaceutical composition of the present invention.

As used herein, the term "treating" refers to all actions that alleviate or beneficially change cancer symptoms by irradiating radiation.

The pharmaceutical composition of the present invention may also be co-administered with other anticancer agent, thereby further increasing its inhibitory effect on the growth of cancer cells and cancer stem cells.

In this regard, the other anticancer agent may be one or more selected from the group consisting of nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, bevacizumab, cisplatin, cetuximab, Viscum album, asparaginase, tretinoin, hydroxycarbamide, dasatinib, estramustine, gemtuzuabozogamicin, ibritumomabtiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, navelbine, fadrozole, tamoxifen, toremifene, testolactone, anastrozole, letrozole, vorozole, bicalutamide, lomustine and carmustine, but is not limited thereto.

In the present invention, the pharmaceutical composition may be in the form of capsule, tablet, granule, injectable solution, ointment, powder or beverage, and may be administered to a human subject.

For use, the pharmaceutical composition of the present invention may be prepared as oral formulations, including powders, granules, capsules, tablets, aqueous suspensions and the like, formulations for external use, suppositories, and sterile injectable solutions, according to respective conventional methods, but is not limited thereto. The pharmaceutical composition of the present invention may contain a pharmaceutically acceptable carrier. For oral administration, the pharmaceutically acceptable carrier may include one or more of binders, lubricants, disintegrants, excipients, solubilizing agents, dispersing agents, stabilizers, suspending agents, pigments, fragrances, and the like. For injection, the pharmaceutically acceptable carrier may include one or more of buffers, preservatives, pain-relieving agents, solubilizing agents, isotonic agents, stabilizers, and the like. For local administration, the pharmaceutically acceptable carrier may include one or more of bases, excipients, lubricants, preservatives, and the like. The pharmaceutical composition according to the present invention may be mixed with the pharmaceutically acceptable carriers as described above to provide various formulations. For example, for oral administration, the pharmaceutical composition of the present invention may be prepared in the form of tablet, troche, capsule, elixir, suspension, syrup, wafer or the like, and for injection, the pharmaceutical composition may be prepared in the form of unit dosage ampoules or multiple dosage containers. In addition, the pharmaceutical composition of the present invention may be prepared as solutions, suspensions, tablets, capsules, sustained-release formulations, or the like.

Meanwhile, examples of carriers, excipients and diluents, which are suitable for formulation, include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, and the like. In addition, the pharmaceutical composition of the present invention may further contain one or more of fillers, anticoagulants, lubricants, wetting agents, fragrances, emulsifiers, preservatives, and the like.

Routes for administration of the pharmaceutical composition according to the present invention include, but are not limited to, oral, intravenous, intramuscular, intra-arterial, intra-marrow, intrathecal, intracardiac, transdermal, subcutaneous, intraperitoneal, intranasal, intestinal, local, sublingual and intrarectal routes. Oral or parenteral administration is preferred.

As used herein, the term "parenteral" is meant to include subcutaneous, intradermal, intravenous, intramuscular, intra-articular, intrabursal, intestinal, intrathecal, intralesional and intracranial injection or infusion techniques. The pharmaceutical composition of the present invention may also be administered in the form of suppositories for rectal administration.

The dose of the pharmaceutical composition of the present invention may vary depending on various factors, including the activity of a particular compound used, the patient's age, body weight, general health, sex, diet, administration time, the route of administration, excretion rate, drug combination, and the severity of a particular disease to be prevented or treated. Although the dose of the pharmaceutical composition varies depending on the patient's condition, body weight, the severity of the disease, the form of drug, the route of administration, and the period of administration, it may be appropriately selected by a person skilled in the art. The pharmaceutical composition may be administered at a dose of 0.0001-50 mg/kg/day or 0.001-50 mg/kg/day. The pharmaceutical composition of the present invention may be administered once or several times a day. The dose does not limit the scope of the present invention in any way. The pharmaceutical composition according to the present invention may be formulated as pills, sugar-coated tablets, capsules, liquids, gels, syrups, slurries, or suspensions.

In one embodiment of the present invention, there is provided a method for preventing or treating cancer, comprising administering to a subject in need of such treatment with an effective amount of a pharmaceutical composition which contains a glucose uptake inhibitor and a sesquiterpene lactone as an active ingredient.

In another embodiment of the present invention, there is provided a method for inhibiting growth of cancer stem cells, comprising administering to a subject in need of such treatment with an effective amount of a pharmaceutical composition which contains a glucose uptake inhibitor and a sesquiterpene lactone as an active ingredient.

DESCRIPTION OF SPECIFIC EMBODIMENTS

Figure 1:
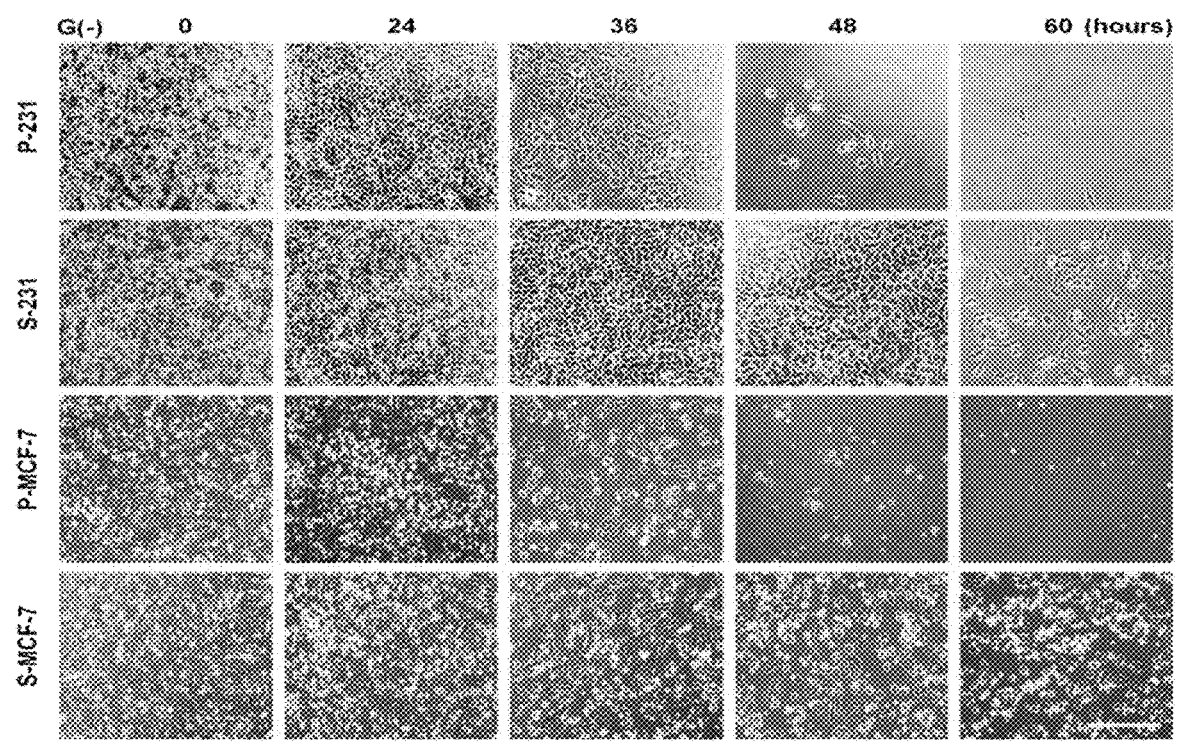
FIG. 1 shows images of microscopic observation performed to examine morphological changes at 0, 24, 36, 48 and 60 hours after replacement with glucose-free medium for parent cell lines (P-231 and P-MCF-7) and selected cell lines (S-231 and S-MCF-7) under glucose deprivation conditions in an example of the present invention.
Figure 2A:
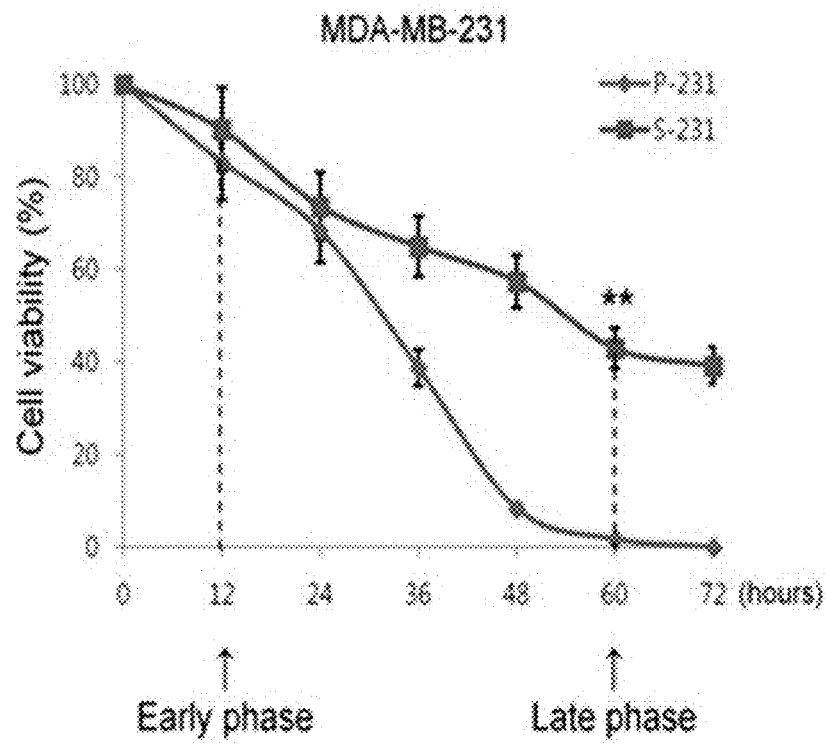
FIGS. 2A and 2B respectively show the results of analyzing the cell viabilities of parent cell lines (P-231 and P-MCF-7) and selected cell lines (S-231 and S-MCF-7) in the early phase and late stage of glucose deprivation by an MTT assay in an example of the present invention.
Figure 2B:
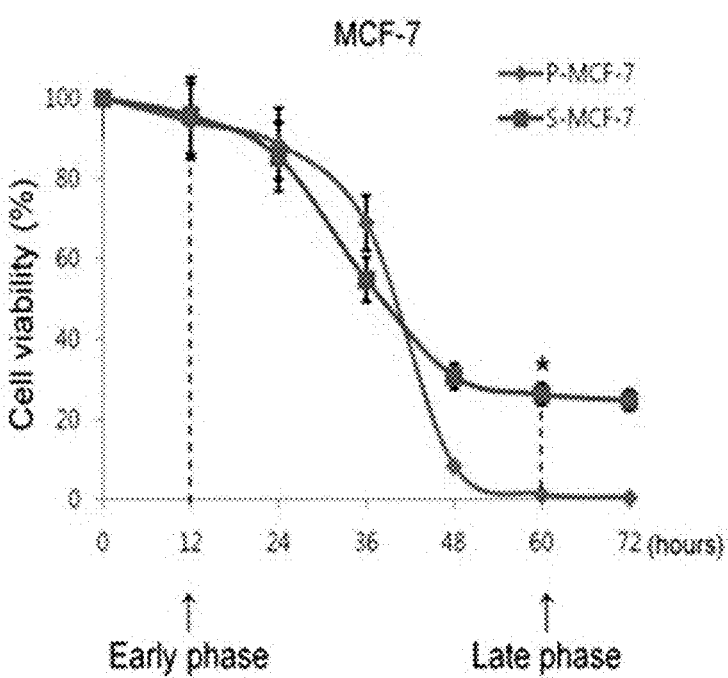

Hereinafter, the present invention will be described in further detail. It will be obvious to those skilled in the art that these examples are for illustrative purposes only and are not intended to limit the scope of the present invention as defined in the claims.

EXAMPLES

Cell Culture

Human breast cancer cell lines (MDA-MB-231 and MCF-7) were obtained from the American Type Culture Collection (ATCC), and then grown in 5% FBS-containing RPMI-1640 medium. All the cell lines were validated by STR DNA fingerprinting using the AmpF_STR Identifier kit. The STR profiles were compared to ATCC fingerprints and Cell Line Integrated Molecular Authentication database (CLIMA) version 0.1.200808 (http://bioinformatics.istge.it/clima/) (Nucleic Acids Research 37:D925-D932 PMCID: PMC2686526).

Cell Viability Assay

Cell viability was analyzed using MTT (3-(4,5-dimethylthiazol-2-yl)-2,5-diphenyltetrazolium bromide).

Microarray Experiment and Data Analysis

From cells obtained after each treatment, total RNA was isolated using mirVana™ miRNA isolation kit (Ambion). Biotin-labeled cRNA was prepared using the Illumina Total Prep RNA amplification kit (Ambion).

Measurement of Intracellular Calcium Concentration

Intracellular free $Ca^{2+}$ concentrations were titrated using the calcium calibration buffer KIT #1 (Life Technologies, Darmstadt, Germany). The fluorescence of cell suspensions was measured using a fluorophore in the presence of different $Ca^{2+}$ and EGTA standard solutions.

Total RNA Extraction and Quantitative RT-PCR (q RT-PCR)

Using an RNeasy Mini kit (Qiagen, Valencia, Calif., USA) and a one-step RT-PCR kit (Qiagen), total RNA was extracted from tumor cells. All data were normalized to GAPDH expression. The primers for SERCA1 (sarcoendoplasmic reticulum calcium transport ATPase 1), SERCA2 and SERCA3 used in RT-PCR are shown in Table 2 below.

TABLE 2

| Gene products | Forward primers | Backward primers |
| --- | --- | --- |
| SERCA1 | GTGATCCGCCAGCTAATG (SEQ ID NO: 1) | CGAATGTCAGGTCCGTCT (SEQ ID NO: 2) |
| SERCA2 | GGTGGTTCATTGCTGCTGAC (SEQ ID NO: 3) | TTTCGGACAAGCTGTTGAGG (SEQ ID NO: 4) |
| SERCA3 | GATGGAGTGAACGACGCA (SEQ ID NO: 5) | CCAGGTATCGGAAGAAGAG (SEQ ID NO: 6) |
| GAPDH | GGTAAGGTCGGAGTCAACGG (SEQ ID NO: 7) | GAGGTCAATGAAGGGGTCATTG (SEQ ID NO: 8) |

Immunoblot Assay

Caspase-3 (Santa Cruz, Calif., USA), caspase-7 (Santa Cruz), caspase-9 (Santa Cruz), Bcl-2 (Santa Cruz), Bcl-$_{xL}$ (Santa Cruz), p-NFκB (Santa Cruz), p-CaMK2α (Abeam), CaMK2α (Abeam), p-IP3R (Abeam), p-IKKα (Abeam), SERCA2 (Abeam) and β-actin (Santa Cruz) were used.

Flow Cytometry for Cell Cycle Analysis

Cells were treated with glucose-free RPMI 1640 medium containing 10% FBS for 40 hours, and then harvested by trypsinization and fixed with 70% ethanol. The cells were stained with a solution containing 40 μg/ml propidium iodide (PI) and 100 μg/ml RNase I in PBS at 37° C. for 30 minutes. The cell cycle distribution was analyzed by a FACS Calibur flow cytometer (BD Biosciences, San Jose, Calif., USA). The percentages of cells in the G0/G1, S and G2/M phases were analyzed using FACS and the DNA software program (FlowJo v9, MacOSX, Tree Star, Ashland, Oreg., USA). This experiment was performed in triplicate, and the results are expressed as mean values.

In Vivo Mouse Xenograft Models

Cancer cells were grown and then injected subcutaneously into the mammary fat pads of 5-6-week-old BALB/c nude mice ($1.0 \times 10^6$ cells/mouse). When the tumor size reached about 100 to 200 mm$^3$, the mice with tumors were randomly grouped (n=8-9/group), and then each of 2-deoxyglucose (2DG, 500 mg/kg), thapsigargin (a non-competitive inhibitor of SERCA; sensitive sarco/endoplasmic reticulum Ca' ATPase, 15 mg/kg), a combination of 2-deoxyglucose+thapsigargin, a combination of 2-deoxyglucose+metformin, or a combination of 2-deoxyglucose+metformin+thapsigargin was administered intraperitoneally or orally to the mice once every 3 days. The tumor size was measured everyday using calipers. The tumor volume was measured using the Equation below. The mice were maintained under specific pathogen-free (SPF) conditions.

Equation $L \times S2/2$ (where $L$ represents the longest diameter, and $S$ represents the shortest diameter).

Selected Cells Resistant to Metabolic Stress have an Increased Potential to Overcome Glucose Deprivation-Induced Apoptosis In order to induce metabolic stress in tumor microenvironments, each type of cancer cells (MDA-MB231 and MCF-7) was cultured for 30 days without replacing or supplementing medium. Although the number of adherent cells decreased with the passage of time, a small number of cells still survived. The number of cells was measured three times consecutively at intervals of 2 days, and when there was no change in the number of cells, the medium was supplemented with fresh medium containing 5% FBS, and the survived cells were established as 'selected cells'.

To evaluate the resistance of the selected cells to metabolic stress, each of the parent cell lines MDA-MB231 (hereinafter referred to as 'P-231') and MCF-7 (hereinafter referred to as 'P-MCF-7'), the cell line selected from P-231 (hereinafter referred to as 'S-231') and the cell line selected from P-MCF-7 (hereinafter referred to as 'S-MCF-7') was exposed to a glucose deprivation environment for various period of times (0, 24, 36, 48 and 60 hours), followed by measurement of cell viability.

As a result, it could be seen that in all the parent cell lines and the selected cell lines, apoptosis increased as the glucose deprivation time increased (FIG. 1). However, when the glucose deprivation condition was maintained for 60 hours, from the results of MTT assay, it could be seen that the parent cell lines were mostly dead, but a significant number of the selected cells still survived (FIGS. 1 to 4).

Figure 3A:
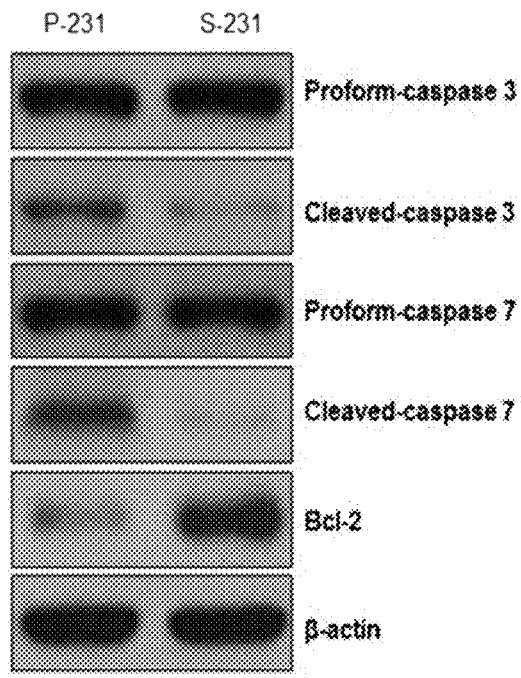
FIGS. 3A and 3B respectively show the results of analyzing the expression levels of apoptosis markers in parent cell lines (P-231 and P-MCF-7) and selected cell lines (S-231 and S-MCF-7) in an example of the present invention.
Figure 3B:
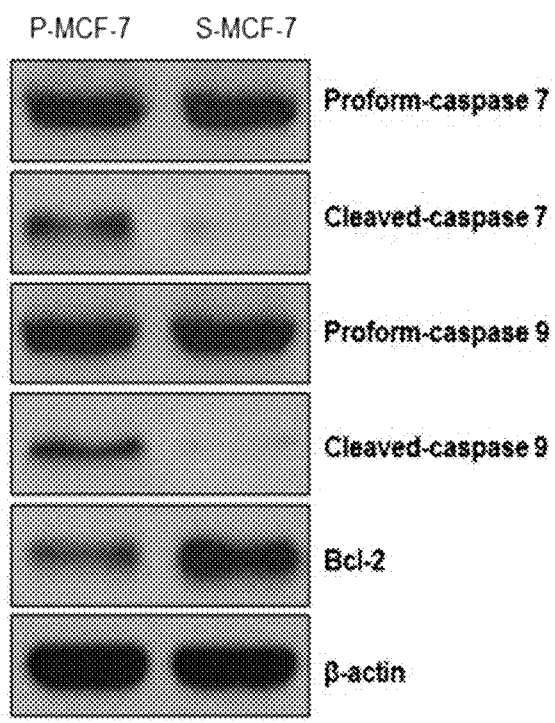
Figure 4:
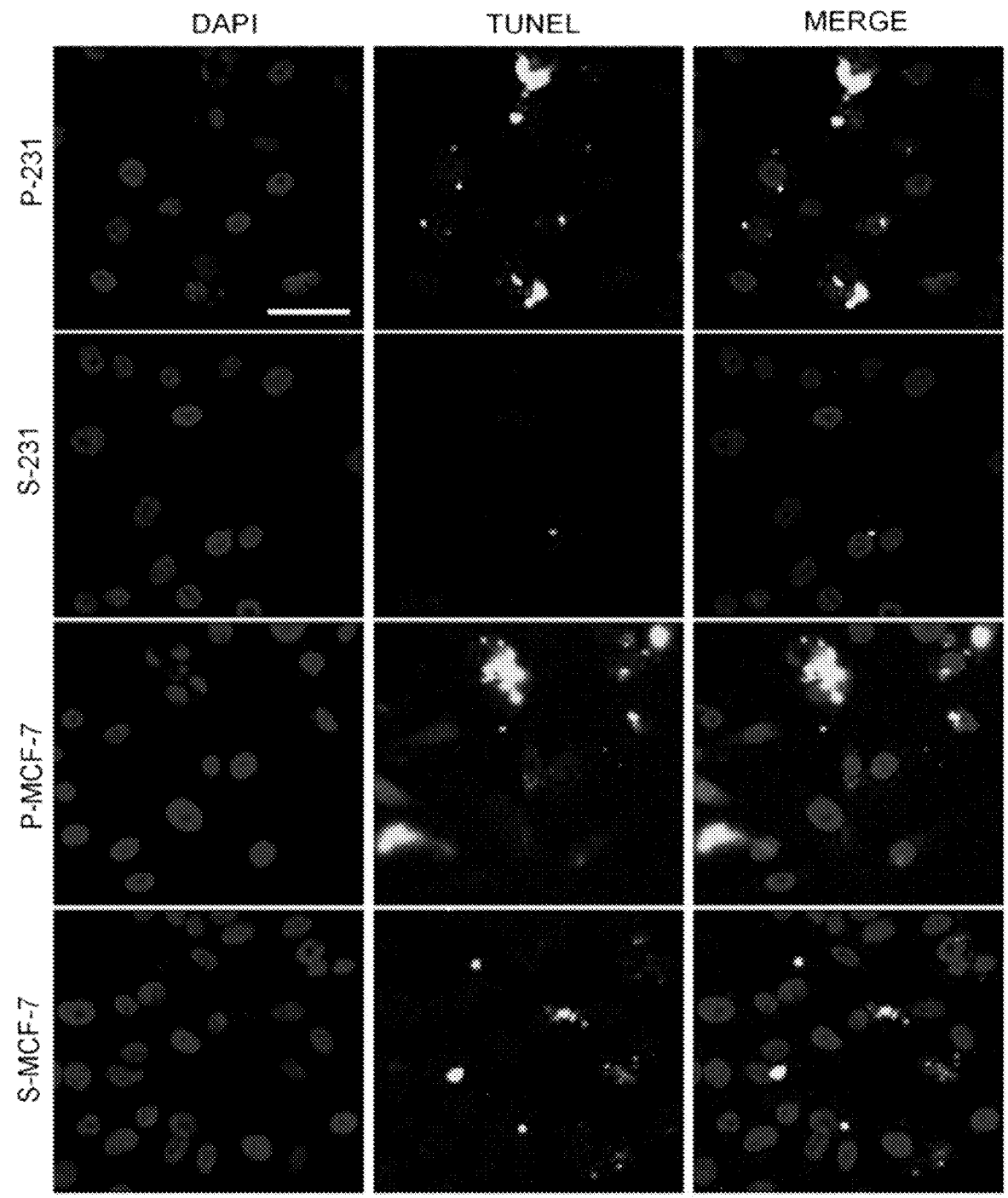
FIG. 4 shows the results of observing nucleic acid fragmentation in parent cell lines (P-231 and P-MCF-7) and selected cell lines (S-231 and S-MCF-7) by a TUNEL assay in an example of the present invention.
Figure 5A:
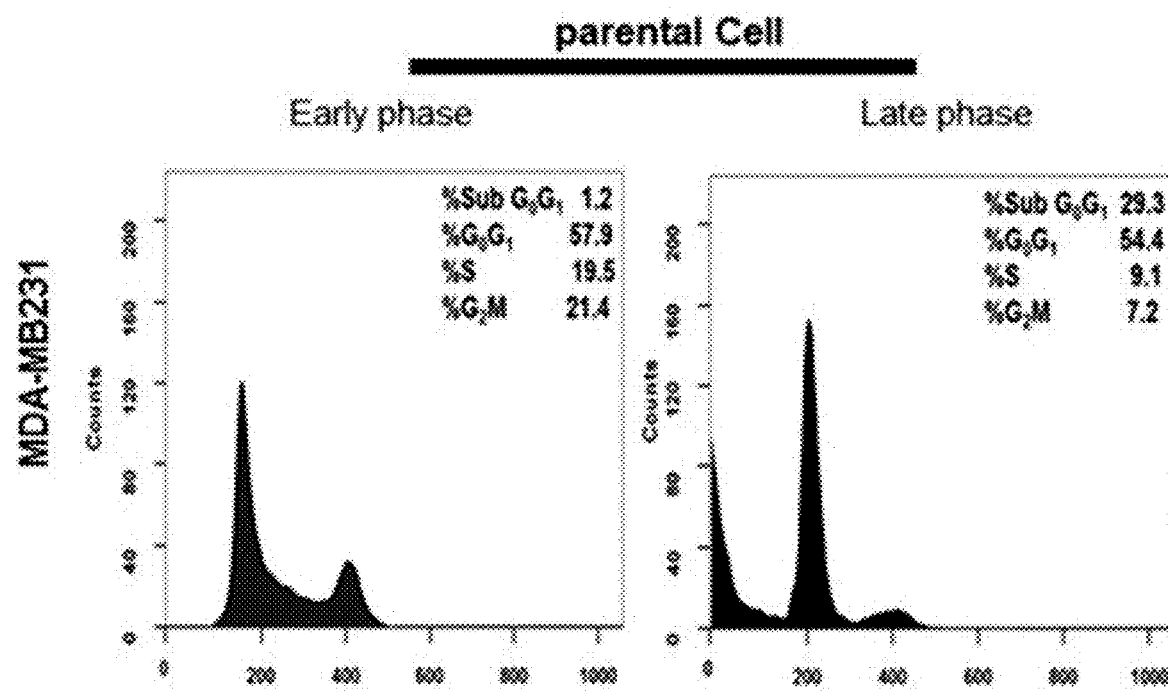
FIGS. 5A, 5B, 5C and 5D respectively show the results of analyzing the cell cycle in parent cell lines (P-231 and P-MCF-7) and selected cell lines (S-231 and S-MCF-7) in the early phase and late stage of glucose deprivation by a TUNEL assay in an example of the present invention.
Figure 5B:
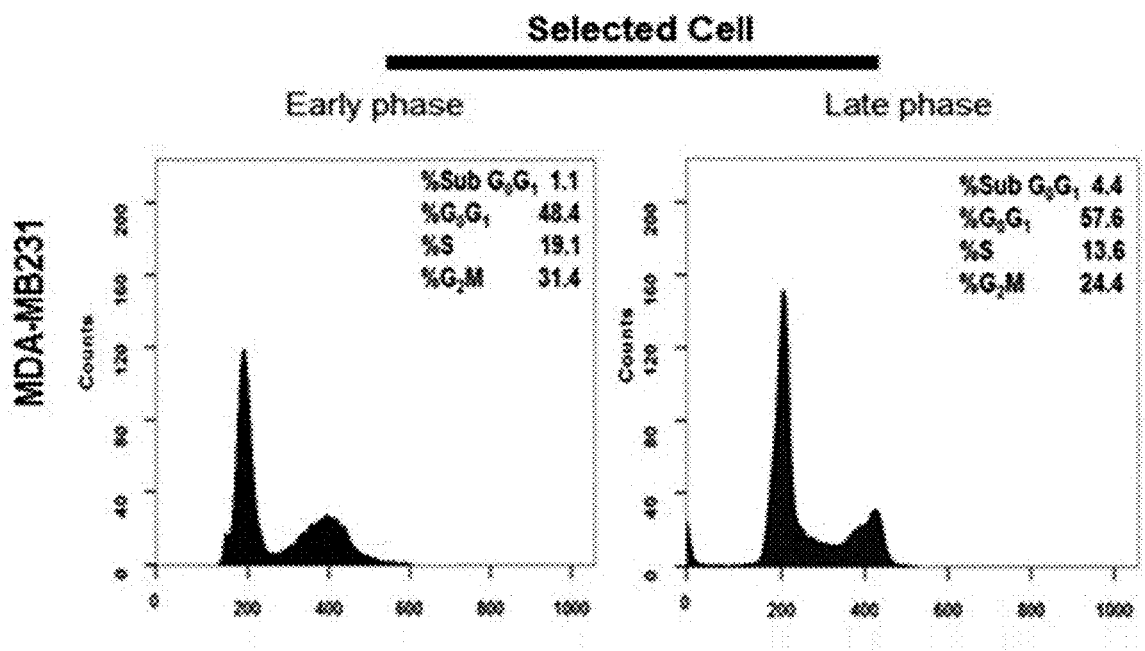
Figure 5C:
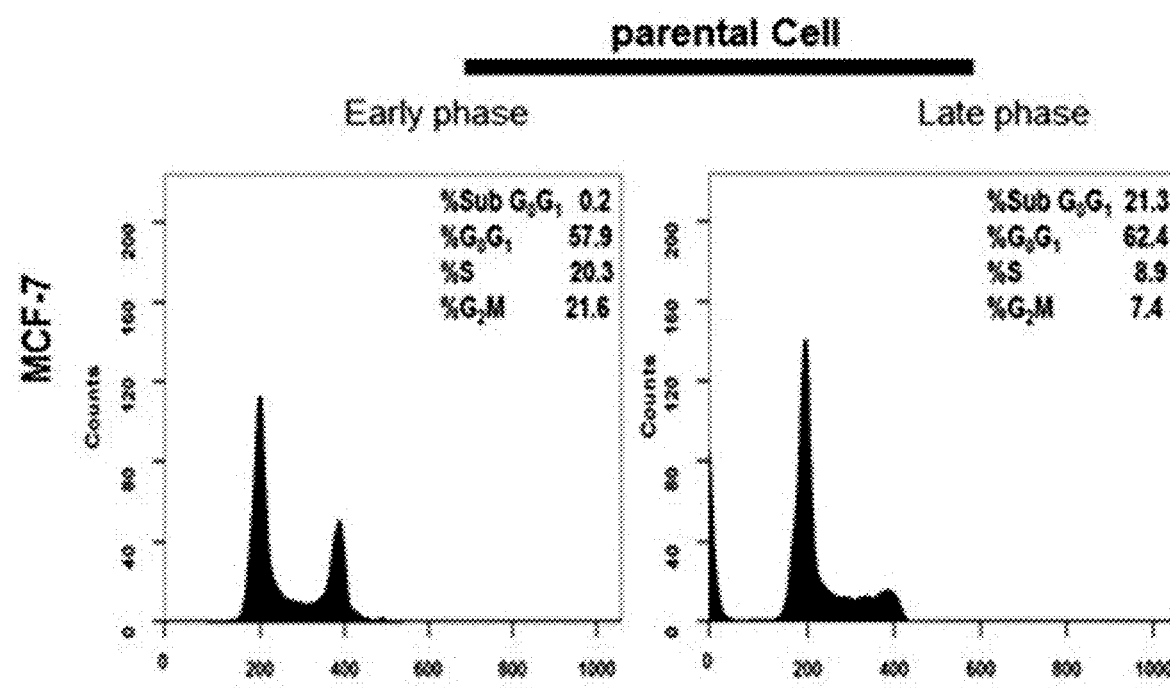
Figure 5D:
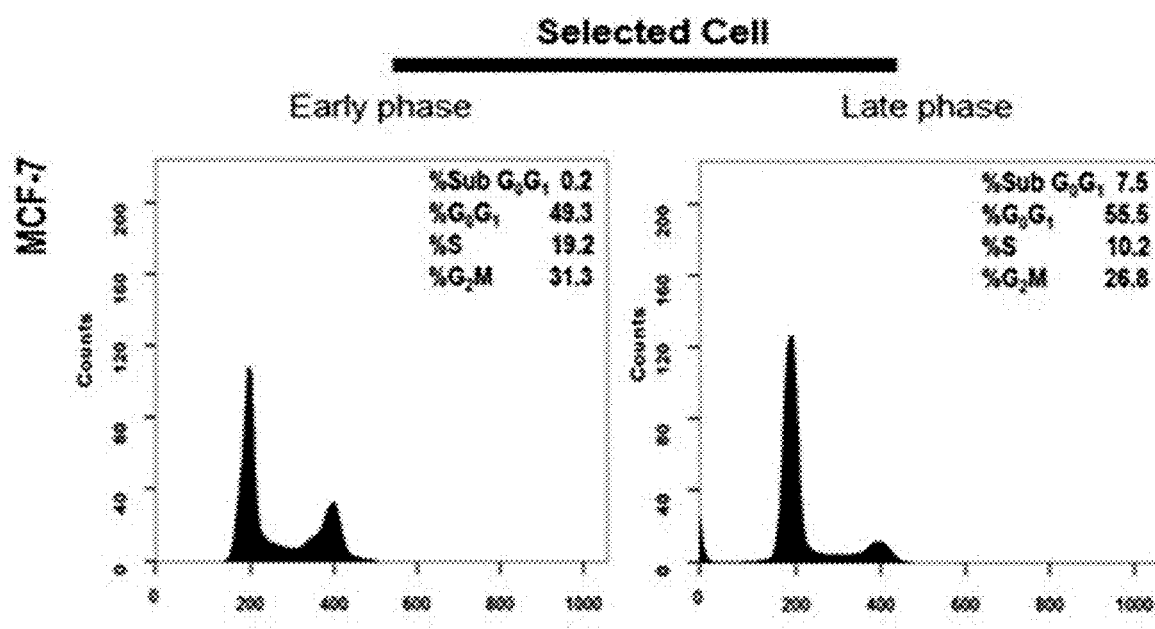

Because activation of the caspase system is a marker of apoptosis, cleavage of caspase-3, caspase-7 and caspase-9 in the parent cell lines and the selected cell lines was examined (FIG. 3). In the MCF-7 cells, cleavage of caspase-9 instead of caspase-3 was measured, because caspase-3 was not expressed therein. The results of TUNEL assay indicated that DNA fragmentation was higher in the parent cell lines than in the selected cell lines and that apoptosis was also higher in the parent cell lines (FIG. 4).

From the results of cell cycle analysis, it could be seen that in the early phase (after 12 hours) under the glucose deprivation condition, there was no significant difference in number between sub-G0/G1 parent cell lines and sub-G0/G1 selected cell lines (P-231 1.2% vs S-231 1.1%; P-MCF-7 0.2% vs S-MCF-7 0.2%), but in the late phase (after 40 hours) under the glucose deprivation condition, sub-G0/G1 parent cell lines were more than sub-G0/G1 selected cell lines (P-231 29.3% vs S-231 4.4%; P-MCF-7 21.3% vs S-MCF-7 7.5%) (FIG. 5).

In addition, it could be seen that the expression level of the anti-apoptosis protein Bcl-2 in the late phase was significantly higher in the selected cell lines than in the parent cell lines (FIG. 3).

Therefore, the above-described results suggest that the selected cell lines are very highly resistant to apoptosis compared to the parent cell lines under the glucose deprivation condition.

However, according to the reference (Lee J, Kee H J, Min S, Park K C, Park S, Hwang T H, Ryu D H, Hwang G S, Cheong J H. Integrated omics-analysis reveals Wnt-mediated NAD+ metabolic reprogramming in cancer stem-like cells, Oncotarget, Vol. 7, No. 30. (2016 Jul. 6)), it can be seen that the selected cell lines S-231 are cancer stem cells.

Stem-Like Cancer Cells were Survived by Transcriptional Reprogramming

Figure 6A:
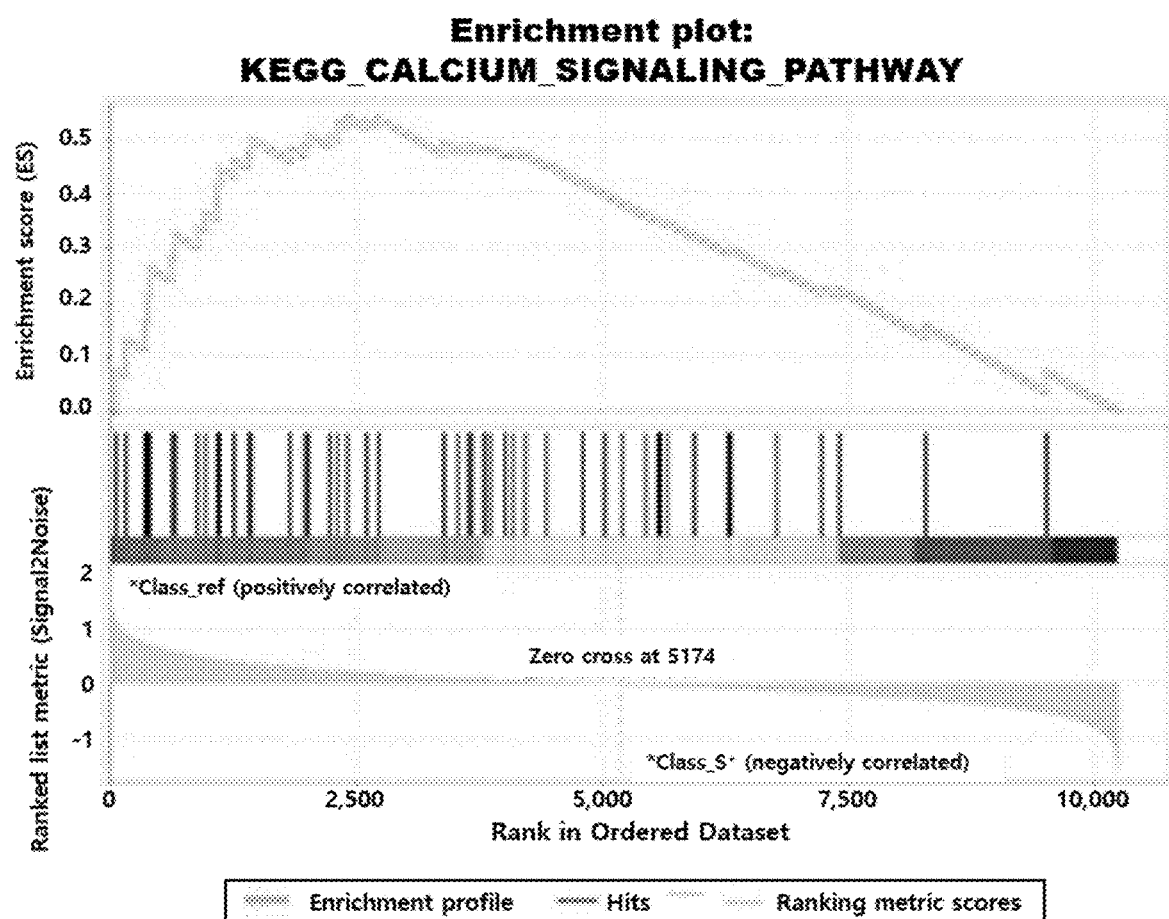
FIGS. 6A, 6B and 6C show the results of whole-genome transcriptional profiling performed on P-231 and S-231 cell lines in an example of the present invention.
Figure 6B:
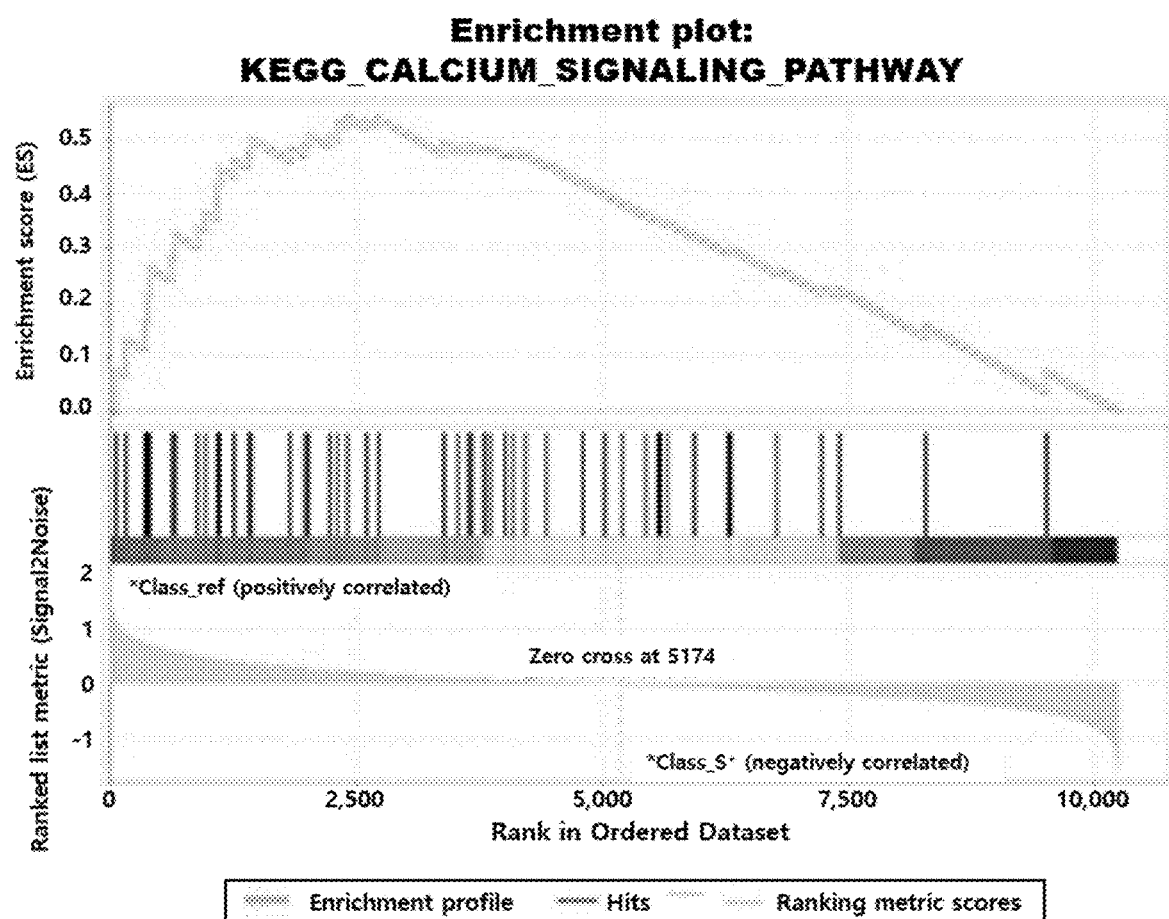
Figure 6C:
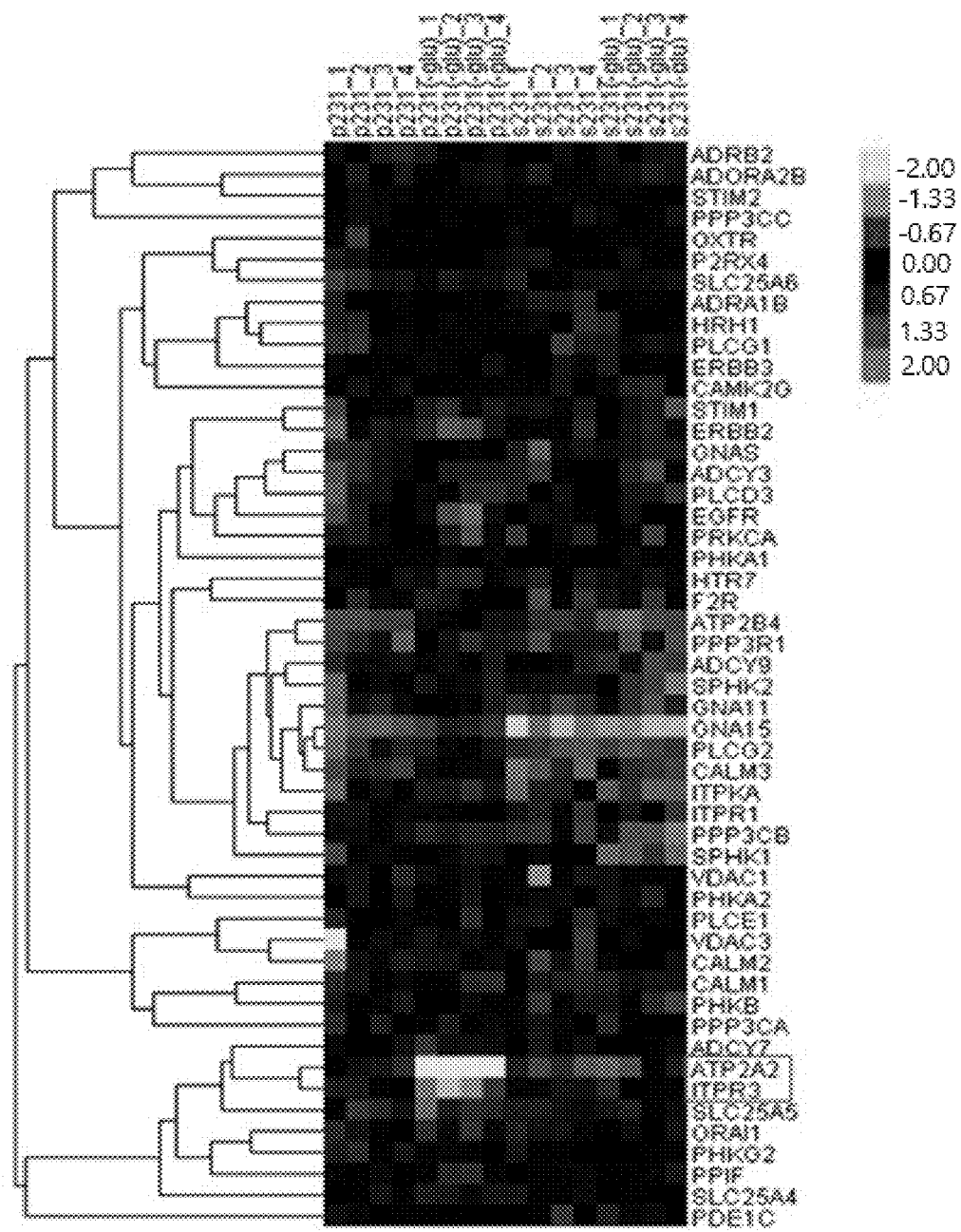

Since gene expression programming is much influenced by environmental signals, it can be predicted that cancer stem cells have stemness by transcriptional reprogramming. Accordingly, whole-genome transcriptional profiling of the P-231 and S-231 cell lines was performed. It could be seen that a significant number of genes in P-231 and S-231 were expressed differently. This suggests that various biological procedures in S-231 are reprogrammed. It could be seen that among the genes showing changed expression levels in S-231, ATP2A2 (SERCA2) and calcium signals were most remarkable (FIG. 6).

Figure 7A:
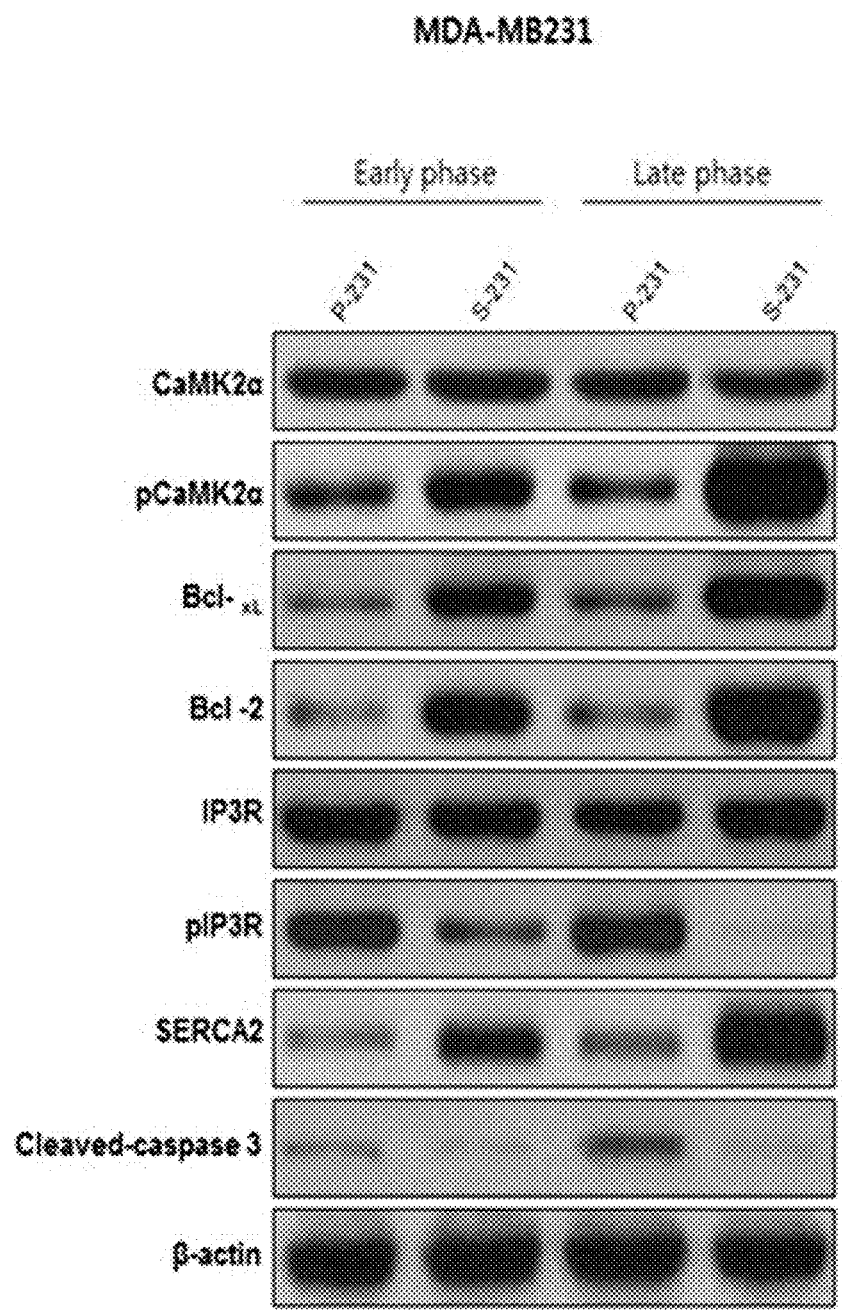
FIGS. 7A and 7B respectively show the results of analyzing the expression levels of anti-apoptosis-related genes, cytoplasmic free calcium-related genes and calcium release genes in parent cell lines (P-231 and P-MCF-7) and selected cell lines (S-231 and S-MCF-7) in the early phase and late stage of glucose deprivation by a Western blot assay in an example of the present invention.
Figure 7B:
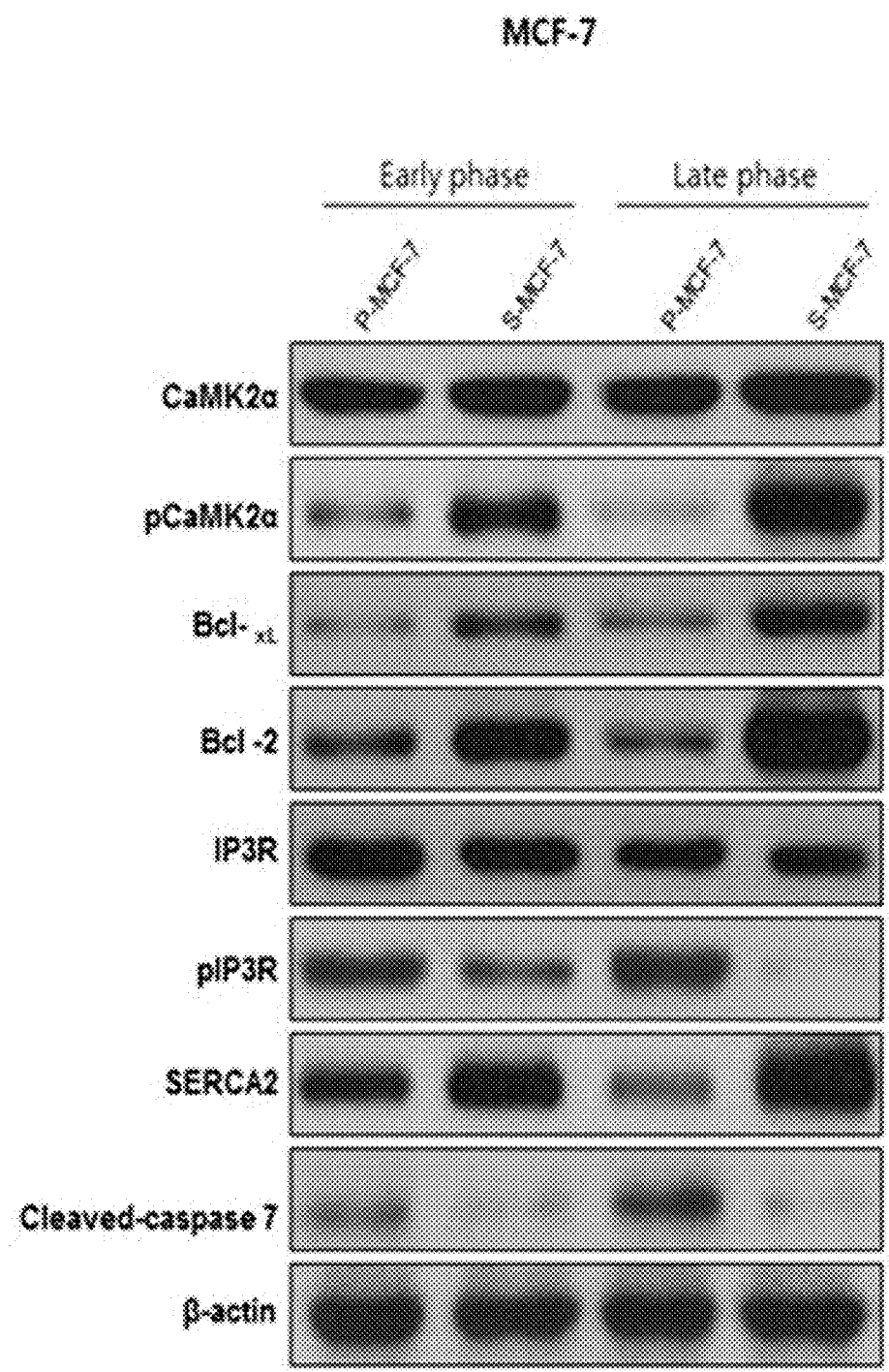

It could be seen that the expression levels of anti-apoptosis-related genes and cytoplasmic free calcium-related genes under the glucose deprivation condition were higher in the selected cell lines than in the parent cell lines and the expression levels of calcium release genes were lower in the selected cell lines (FIG. 7).

Figure 8A:
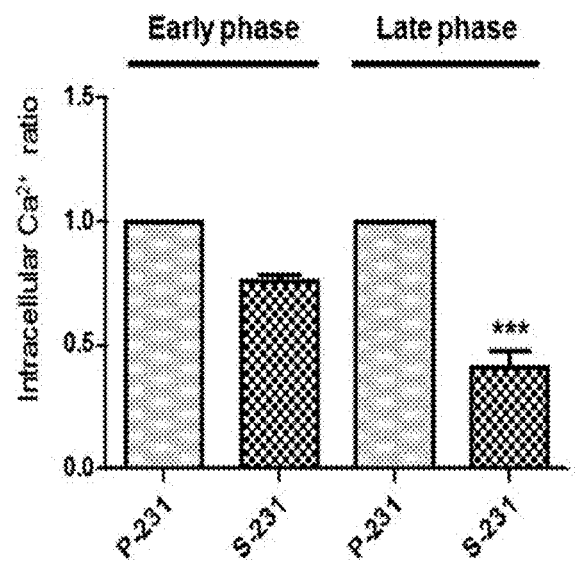
FIGS. 8A and 8B respectively show the ratio of the intracellular calcium concentration of selected cell lines (S-231 and S-MCF-7) to that of parent cell lines (P-231 and P-MCF-7) in the early phase and late stage of glucose deprivation in an example of the present invention.
Figure 8B:
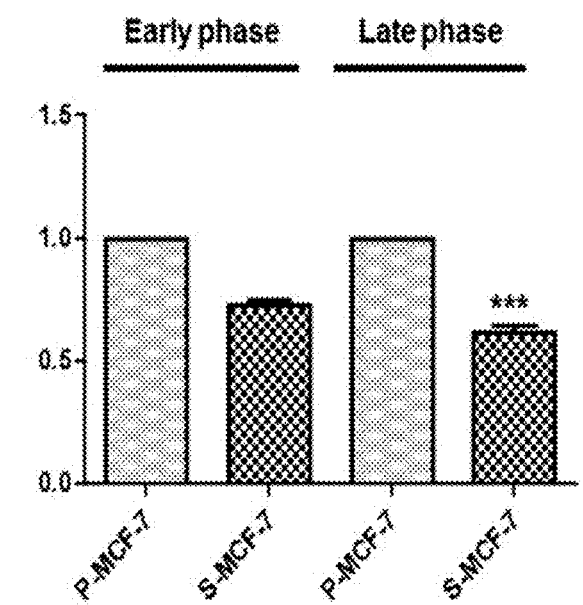
Figure 9:
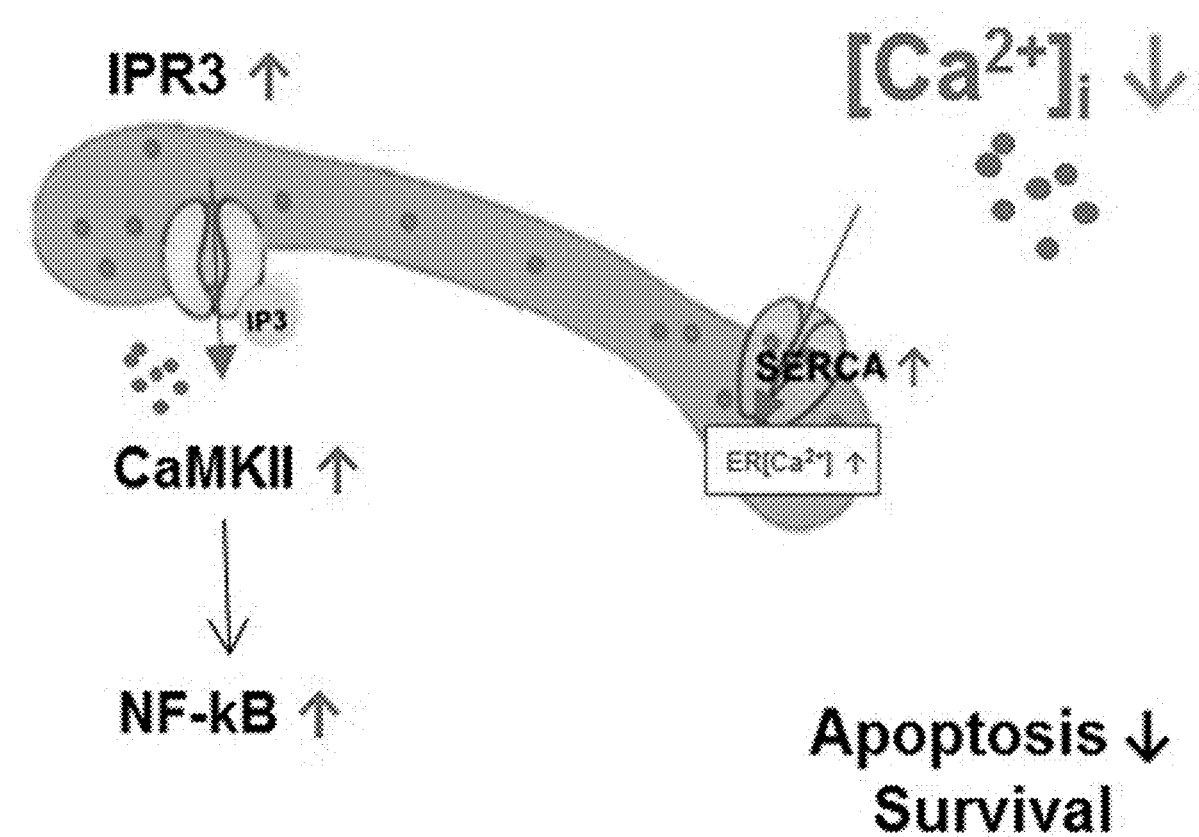
FIG. 9 shows a schematic view of signaling for the ability to restore cytoplasmic free calcium in selected cell lines (S-231 and S-MCF-7).
Figure 10A:
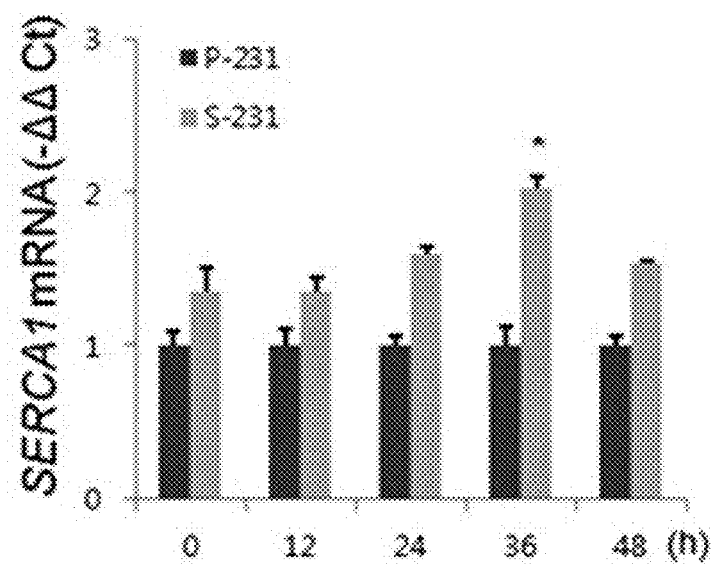
FIGS. 10A, 10B, 10C, 10D, 10E and 10F respectively show the results of comparing the mRNA expression levels of SERCA families 1, 2 and 3 as a function of the time of glucose deprivation between selected cell lines (S-231 and S-MCF-7) and parent cell lines (P-231 and P-MCF-7) by qPCR in an example of the present invention.
Figure 10B:
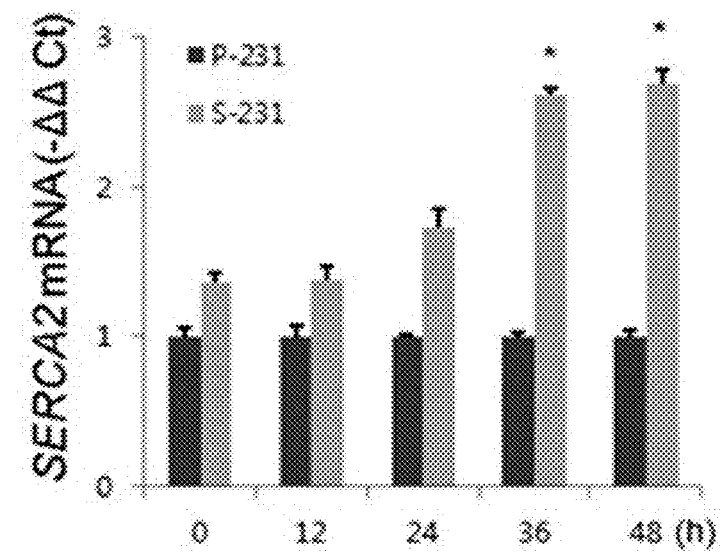
Figure 10C:
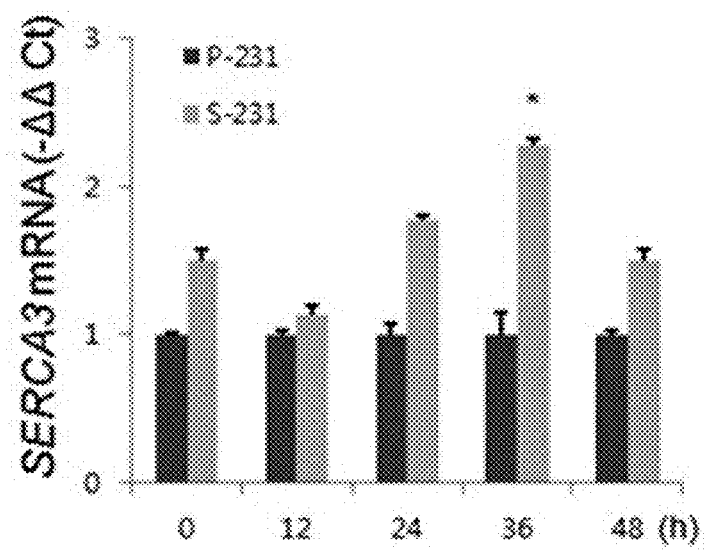
Figure 10D:
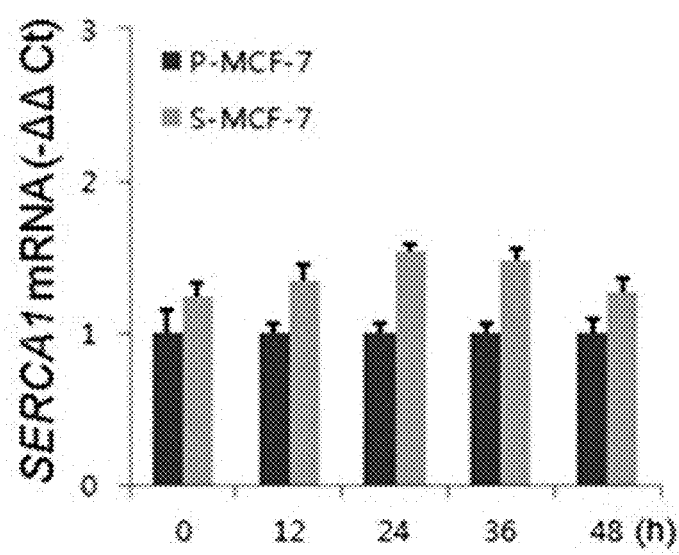
Figure 10E:
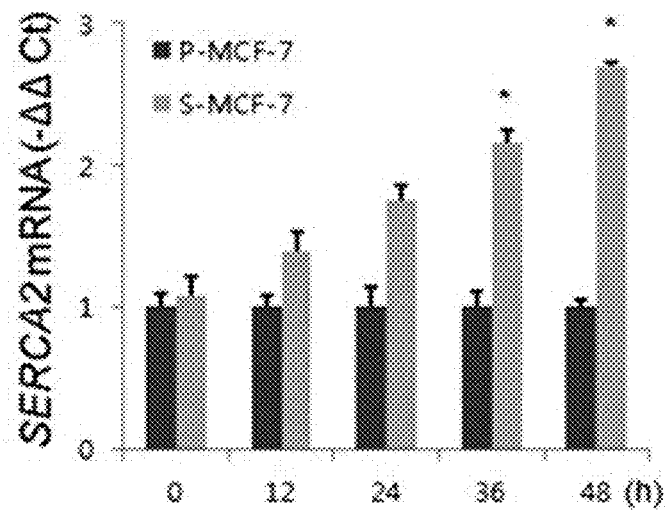
Figure 10F:
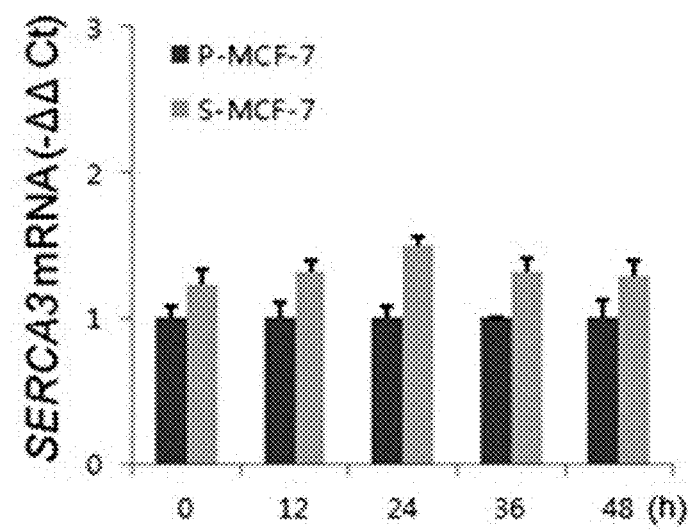

However, it could be seen that in the early and late phages of glucose deprivation, the concentration of cytoplasmic free calcium in the selected cell lines was decreased (FIGS. 8A and 8B), but the selected cell lines had an excellent ability to restore cytoplasmic free calcium through CaMK2a and SERCA (FIG. 9).

From the above-described results, it can be seen that the selected cells can survive for a long period of time by transcriptional reprogramming through CaMK2α-mediated SERCA when glucose deprivation is applied thereto.

Meanwhile, since SERCA, a main transporter of $Ca^{2+}$, removes $Ca^{2+}$ from the cytoplasm, the expression level of SERCA under the glucose deprivation condition was measured. It could be seen that there was no change in the expression level of SERCA in the P-231 cells under the glucose deprivation condition, but the expression level of SERCA in the S-231 cells increased depending on the deprivation time. Among three kinds of SERCA, the expression level of SERCA2 mRNA significantly increased (FIGS. 10A to 10F). This could also be observed in the S-MCF-7 cells.

Figure 11A:
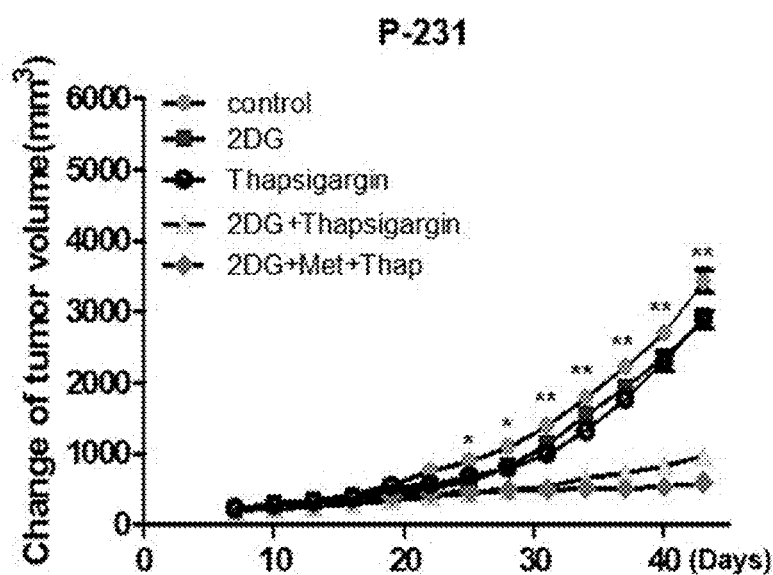
FIGS. 11A and 11B respectively show the changes in tumor volume after treatment with 2-deoxyglucose (2DG), thapsigargin, 2-deoxyglucose+thapsigargin (2DG+Thapsigargin), 2-deoxyglucose+metformin (2DG+Metformin), and 2-deoxyglucose+thapsigargin+metformin (2DG+Met+Thap) in P-231 or S-231 xenograft mouse models in an example of the present invention.
Figure 11B:
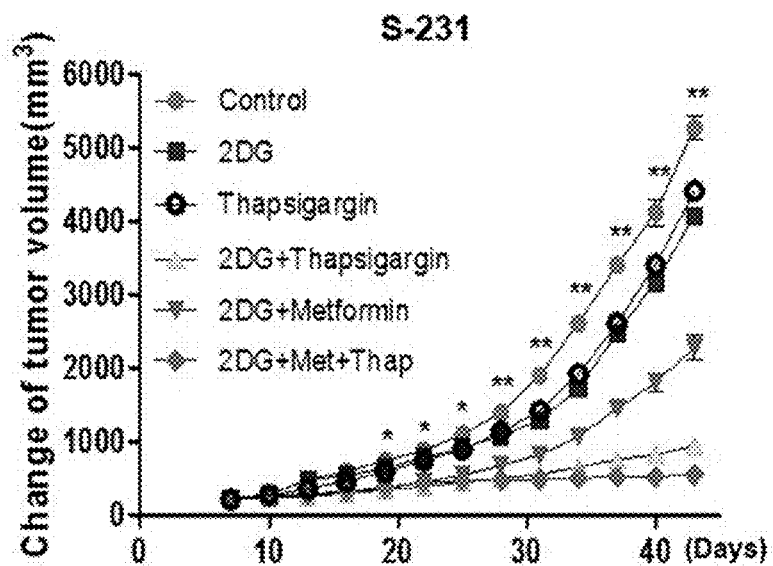
Figure 12A:
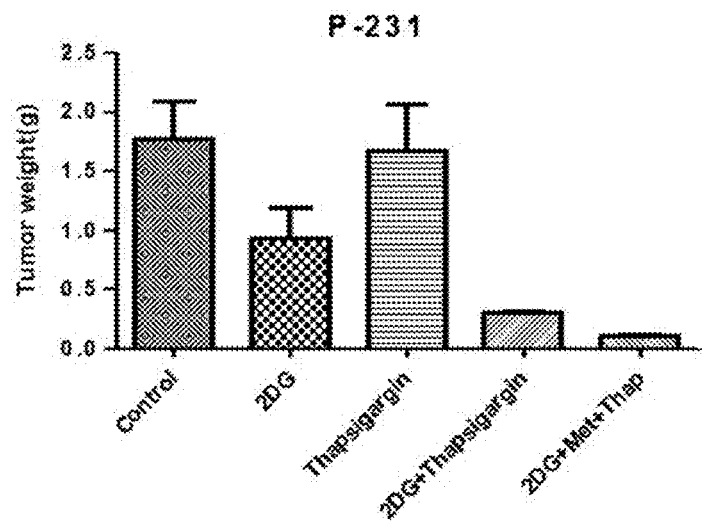
FIGS. 12A and 12B respectively show the changes in tumor weight after treatment with 2-deoxyglucose (2DG), thapsigargin, 2-deoxyglucose+thapsigargin (2DG+Thapsigargin), 2-deoxyglucose+metformin (2DG+Metformin), and 2-deoxyglucose+thapsigargin+metformin (2DG+Met+Thap) in P-231 or S-231 xenograft mouse models in an example of the present invention.
Figure 12B:
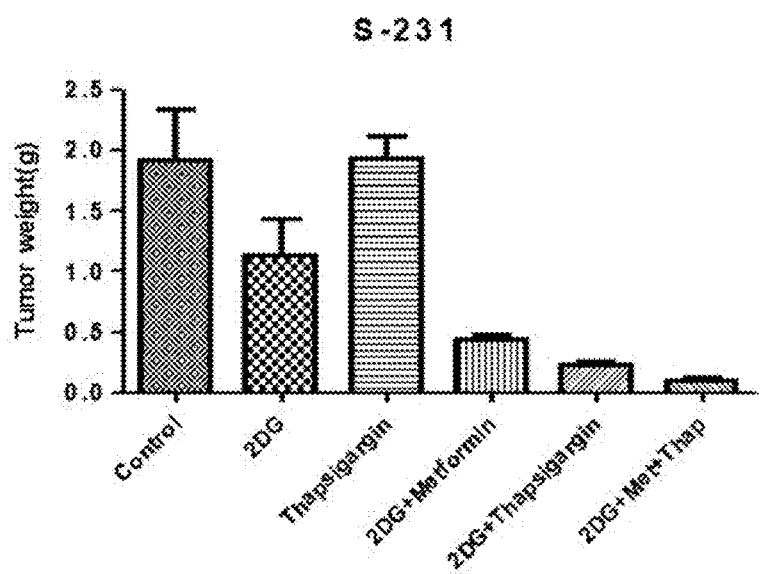

SERCA Inhibitor Combined with Glucose Deprivation-Mimetic Suppresses Tumor Progression in Mouse Xenograft Tumor Models The mouse xenograft tumor models prepared as described above were treated with each of 2-deoxyglucose (2DG), thapsigargin, 2-deoxyglucose (2DG)+thapsigargin, 2-deoxyglucose (2DG)+metformin, and 2-deoxyglucose (2DG)+metformin (Met)+thapsigargin (Thap). To form an in vivo glucose inhibitory environment, the mouse xenograft tumor models were injected with the metabolic inhibitor 2-deoxyglucose (2DG) to induce energy stress, followed by treatment with thapsigargin. As a result, it could be seen that, in both the P-231 and S-231 xenograft models co-administered with 2-deoxyglucose (2DG) and thapsigargin, the volume and weight of tumors significantly decreased compared to those in an untreated control group or the group treated with metabolic inhibitor 2-deoxyglucose (2DG) alone (FIGS. 11 and 12). In addition, in the models xenografted with the cancer stem cells S-231, it could be seen that the effect of reducing the tumor volume and weight was significantly better in the group co-administered with 2-deoxyglucose and thapsigargin than in the group co-administered with 2-deoxyglucose and metformin (FIG. 11B).

In addition, when metformin was added to 2-deoxyglucose and thapsigargin, it could be seen that the tumor volume and weight more significantly decreased on both the P-231 and S-231 xenograft models (FIGS. 11 and 12).

The above-described results suggest that when 2-deoxyglucose and thapsigargin are co-administered according to the present invention, the effect of reducing the tumor volume and weight is significantly better than when 2-deoxyglucose and thapsigargin are administered alone, and that when a combination of 2-deoxyglucose, thapsigargin and metformin is administered, the effect of reducing the tumor volume and weight further increases. Furthermore, it could be seen that the effect of reducing the tumor volume and weight was better particularly in the model xenografted with the cancer stem cells S-231.

Figure 13A:
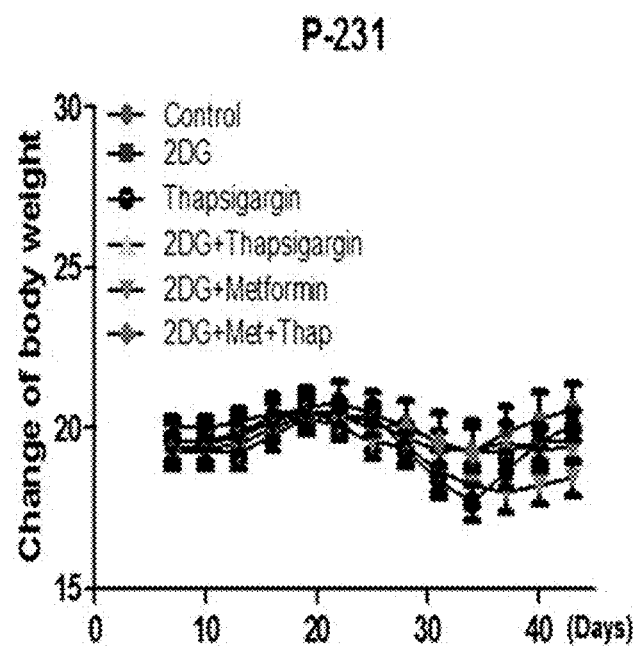
FIGS. 13A and 13B respectively show the changes in mouse body weight after treatment with 2-deoxyglucose (2DG), thapsigargin, 2-deoxyglucose+thapsigargin (2DG+Thapsigargin), 2-deoxyglucose+metformin (2DG+Metformin), and 2-deoxyglucose+thapsigargin+metformin (2DG+Met+Thap) in P-231 or S-231 xenograft mouse models in an example of the present invention.
Figure 13B:
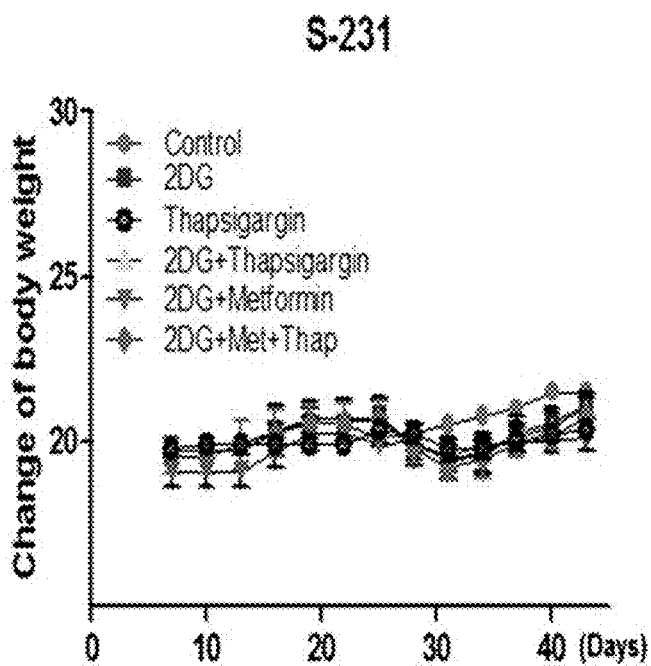

Meanwhile, it can be seen that when the mouse xenograft tumor models were co-administered with 2-deoxyglucose and thapsigargin or co-administered with 2-deoxyglucose, thapsigargin and metformin, the body weights of these models did not significantly change compared to that of the control (FIGS. 13A and 13B). This suggests that co-administration of 2-deoxyglucose and thapsigargin or co-administration of 2-deoxyglucose, thapsigargin and metformin is not toxic to the subjects, like administration of each of 2-deoxyglucose, thapsigargin and metformin.

As described above, the pharmaceutical composition according to the present invention is capable of effectively inhibiting the growth of not only cancer cells but also cancer stem cells by co-administering a glucose uptake inhibitor and a sesquiterpene lactone, thereby preventing and/or treating cancer, and furthermore, preventing the resistance, metastasis and recurrence of cancer.

Figure 14:
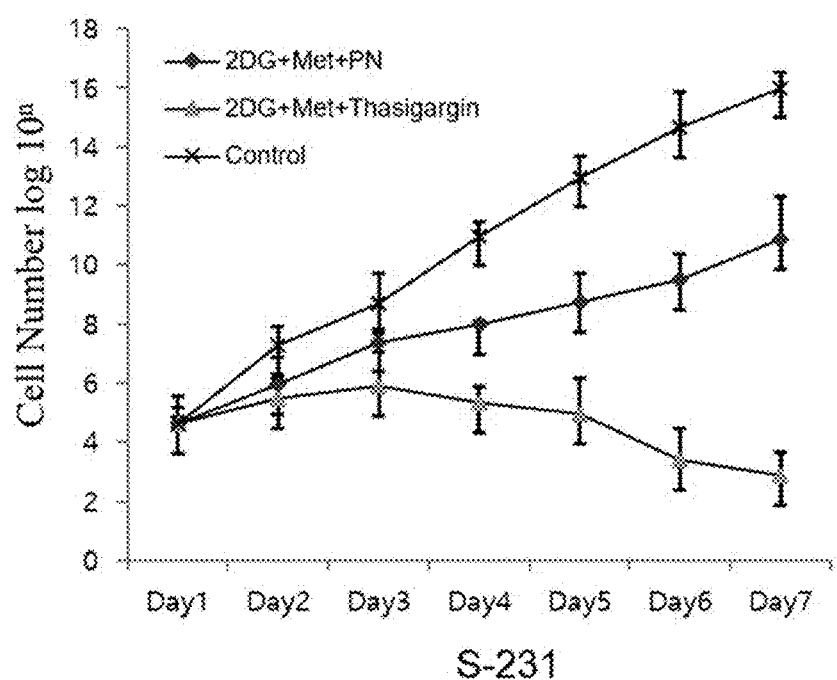
FIG. 14 shows the results of selective cancer treatment effect of thapsigargin among the sesquiterpene lactones in an example of the present invention.

Selective Cancer Treatment Effect of Thapsigargin Among the Sesquiterpene Lactones A distinctive effect on the cancer treatment of thapsigargin, one of the sesquiterpene lactone families, was confirmed when the combination of 2-deoxyglucose and thapsigargin, or 2-deoxyglucose, thapsigargin, and metformin. In order to confirm this, as in the case of thapsigargin, when parthenolide (PN) which is one of the sesquiterpene lactone families was selected and administered in combination with metformin, the effect of inhibiting the proliferation of S-231 was measured (FIG. 14). As a result, it was confirmed that 2-deoxyglucose+metformin+parthenolide (2DG+Met+PN) had insufficient inhibitory effect on cell proliferation. In addition, it was confirmed that 2-deoxyglucose+metformin+thapsigargin (2DG+Met+Thap) was superior in inhibiting cell proliferation. Therefore, when the sesquiterpene lactone compound is used in combination with the 2-deoxyglucose, not all of the sesquiterpene lactones families is excellent in the cancer treatment effect. Among the sesquiterpene lactone families, it was found that the thapsigargin was distinctively effective for cancer treatment.

What is claimed is:

1. A method for treating breast cancer, comprising administering to a subject in need of such treatment with an effective amount of a pharmaceutical composition which contains 2-deoxyglucose (2-DG) and thapsigargin as an active ingredient.

2. The method of claim 1, wherein the 2-DG and thapsigargin are contained at a weight ratio of 1:0.5 to 100.

3. The method of claim 1, which further contains metformin.

4. The method of claim 1, wherein the cancer comprises cancer stem cells.

5. A method for inhibiting growth of breast cancer stem cells, comprising administering to a subject in need of such treatment with an effective amount of a pharmaceutical composition which contains 2-DG and thapsigargin as an active ingredient.

6. The method of claim 5, which further contains metformin.

* * * * *

SEQUENCE LISTING

```
<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: SERCA1-Forward primers

<400> SEQUENCE: 1
gtgatccgcc agctaatg                                                 18

<210> SEQ ID NO 2
<211> LENGTH: 18
<212> TYPE: DNA
<213> ORGANISM: Artificial Sequence
<220> FEATURE:
<223> OTHER INFORMATION: SERCA1-Backward primers

<400> SEQUENCE: 2
cgaatgtcag gtccgtct                                                 18

<210> SEQ ID NO 3
<211> LENGTH: 20
<212> TYPE: DNA
<213> ORGANISM: Artificial Sequence
<220> FEATURE:
<223> OTHER INFORMATION: SERCA2-Forward primers
```

-continued

```
<400> SEQUENCE: 3
ggtggttcat tgctgctgac                                              20

<210> SEQ ID NO 4
<211> LENGTH: 20
<212> TYPE: DNA
<213> ORGANISM: Artificial Sequence
<220> FEATURE:
<223> OTHER INFORMATION: SERCA2-Backward primers

<400> SEQUENCE: 4
tttcggacaa gctgttgagg                                              20

<210> SEQ ID NO 5
<211> LENGTH: 18
<212> TYPE: DNA
<213> ORGANISM: Artificial Sequence
<220> FEATURE:
<223> OTHER INFORMATION: SERCA3-Forward primers

<400> SEQUENCE: 5
gatggagtga acgacgca                                                18

<210> SEQ ID NO 6
<211> LENGTH: 19
<212> TYPE: DNA
<213> ORGANISM: Artificial Sequence
<220> FEATURE:
<223> OTHER INFORMATION: SERCA3-Backward primers

<400> SEQUENCE: 6
ccaggtatcg gaagaagag                                               19

<210> SEQ ID NO 7
<211> LENGTH: 20
<212> TYPE: DNA
<213> ORGANISM: Artificial Sequence
<220> FEATURE:
<223> OTHER INFORMATION: GAPDH-Forward primers

<400> SEQUENCE: 7
ggtaaggtcg gagtcaacgg                                              20

<210> SEQ ID NO 8
<211> LENGTH: 22
<212> TYPE: DNA
<213> ORGANISM: Artificial Sequence
<220> FEATURE:
<223> OTHER INFORMATION: GAPDH-Backward primers

<400> SEQUENCE: 8
gaggtcaatg aagggcat tg                                             22
```